United States Patent
Fojtik et al.

(10) Patent No.: US 10,806,348 B2
(45) Date of Patent: Oct. 20, 2020

(54) METHODS, APPARATUS AND SYSTEMS FOR FACILITATING INTRODUCTION OF SHAPED MEDICAL INSTRUMENTS INTO THE BODY OF A SUBJECT

(71) Applicant: CIRCA Scientific, Inc., Englewood, CO (US)

(72) Inventors: Shawn P. Fojtik, Park City, UT (US); Leroy D. Jutte, Highlands Ranch, CO (US)

(73) Assignee: CIRCA Scientific, Inc., Englewood, CO (US)

( * ) Notice: Subject to any disclaimer, the term of this patent is extended or adjusted under 35 U.S.C. 154(b) by 341 days.

(21) Appl. No.: 15/832,538

(22) Filed: Dec. 5, 2017

(65) Prior Publication Data

US 2018/0092546 A1   Apr. 5, 2018

Related U.S. Application Data

(63) Continuation of application No. 13/101,640, filed on May 5, 2011, now Pat. No. 9,833,149, which is a
(Continued)

(51) Int. Cl.
*A61B 5/00* (2006.01)
*A61B 5/01* (2006.01)
(Continued)

(52) U.S. Cl.
CPC .......... *A61B 5/015* (2013.01); *A61B 17/0218* (2013.01); *A61M 25/002* (2013.01);
(Continued)

(58) Field of Classification Search
CPC ......... A61B 5/01; A61B 5/015; A61B 5/6853; A61B 5/6858; A61B 5/6859; A61B 17/0218; A61M 25/01; A61M 25/002
See application file for complete search history.

(56) References Cited

U.S. PATENT DOCUMENTS 2,756,752 A   7/1956   Scherlis
D237,116 S   10/1975   Ekbladh
(Continued)

FOREIGN PATENT DOCUMENTS

EP   1 504 725   2/2005
JP   HEI 01-107307   7/1989
(Continued)

OTHER PUBLICATIONS

State Intellectual Property Office of the People's Republic of China, Notification of the First Office Action, CN App. No. 201711418339.3, dated Sep. 26, 2018.
(Continued)

*Primary Examiner* — Max F Hindenburg
(74) *Attorney, Agent, or Firm* — Durham Jones & Pinegar, P.C., Intellectial Property Law Group

(57) ABSTRACT

A method for introducing a shaped portion of an elongate medical instrument into a body of a subject includes at least partially straightening the shaped portion of the elongate medical instrument. A retention element may be introduced into an interior of the shaped portion of the elongate medical instrument to place and/or maintain the shaped portion in an at least partially straightened configuration. Such straightening may be accomplished without application of external force to an exterior of the shaped portion. With the retention element in place, the shaped portion may be introduced to a desired location within a hollow interior of an internal organ. The retention element may then be removed to enable the shaped portion to return to its desired shape. A straightening apparatus includes a retention element that can place and/or maintain a shaped portion of an elongate medical instrument in an at least partially straightened configuration without assistance of external force.

19 Claims, 7 Drawing Sheets

Related U.S. Application Data continuation-in-part of application No. 12/406,771, filed on Mar. 18, 2009, now Pat. No. 9,155,476.

(60) Provisional application No. 61/037,624, filed on Mar. 18, 2008.

(51) Int. Cl.

| | | |
|---|---|---|
| *A61M 25/00* | (2006.01) | |
| *A61M 25/01* | (2006.01) | |
| *A61B 17/02* | (2006.01) | |
| A61B 18/00 | (2006.01) | |
| A61B 17/00 | (2006.01) | |

(52) U.S. Cl.
CPC .............. *A61M 25/01* (2013.01); *A61B 5/01* (2013.01); *A61B 5/6853* (2013.01); *A61B 5/6858* (2013.01); *A61B 5/6859* (2013.01); *A61B 2017/00088* (2013.01); *A61B 2017/00862* (2013.01); *A61B 2018/00797* (2013.01); *A61B 2562/0271* (2013.01)

(56) References Cited

U.S. PATENT DOCUMENTS

| | | | |
|---|---|---|---|
| D282,965 S | 3/1986 | Wellenstam | |
| 4,676,249 A * | 6/1987 | Arenas | A61M 25/09025 600/434 |
| 5,170,803 A | 12/1992 | Hewson et al. | |
| 5,211,183 A | 5/1993 | Wilson | |
| 5,325,848 A | 7/1994 | Adams et al. | |
| 5,382,231 A | 1/1995 | Shlain | |
| 5,391,155 A | 2/1995 | Sachse | |
| 5,536,274 A | 7/1996 | Neuss | |
| 5,673,695 A | 10/1997 | McGee et al. | |
| 5,680,860 A | 10/1997 | Imran | |
| D389,365 S | 1/1998 | Lipson | |
| 5,800,413 A | 9/1998 | Swartz et al. | |
| 5,803,902 A | 9/1998 | Sienkiewicz et al. | |
| 5,807,339 A * | 9/1998 | Bostrom | A61M 25/0041 604/164.01 |
| 6,015,382 A | 1/2000 | Zwart et al. | |
| 6,080,118 A | 6/2000 | Blythe | |
| 6,080,160 A | 6/2000 | Chen et al. | |
| 6,090,050 A | 7/2000 | Constantinides | |
| 6,106,522 A * | 8/2000 | Fleischman | A61B 5/0422 606/41 |
| 6,371,928 B1 | 4/2002 | Mcfann et al. | |
| 6,432,041 B1 | 8/2002 | Taniguchi et al. | |
| 6,589,259 B1 | 7/2003 | Solingen | |
| 6,939,313 B2 | 9/2005 | Saadat et al. | |
| 7,140,766 B2 | 11/2006 | Glukhovsky et al. | |
| 7,293,915 B2 | 11/2007 | Chen | |
| 7,361,180 B2 | 4/2008 | Saadat et al. | |
| 7,621,908 B2 | 11/2009 | Miller | |
| D611,601 S | 3/2010 | Tamai et al. | |
| D624,651 S | 9/2010 | Leroy et al. | |
| D624,652 S | 9/2010 | Carus et al. | |
| D625,809 S | 10/2010 | Cushieri et al. | |
| D625,812 S | 10/2010 | Dapri et al. | |
| D625,813 S | 10/2010 | Dapri et al. | |
| D626,226 S | 10/2010 | Carus et al. | |
| D626,227 S | 10/2010 | Leroy et al. | |
| 7,819,817 B2 | 10/2010 | Rahn | |
| 9,155,476 B2 | 10/2015 | Fojtik | |
| 9,833,149 B2 * | 12/2017 | Fojtik | A61B 5/015 |
| 2002/0133223 A1 | 9/2002 | Vito et al. | |
| 2003/0013985 A1 | 1/2003 | Saadat | |
| 2004/0073132 A1 | 4/2004 | Maahs et al. | |
| 2004/0133273 A1 | 7/2004 | Cox | |
| 2004/0176699 A1 | 9/2004 | Walker et al. | |
| 2004/0186469 A1 | 9/2004 | Woloszko et al. | |
| 2004/0215296 A1 | 10/2004 | Ganz et al. | |
| 2005/0033334 A1 | 2/2005 | Santra et al. | |
| 2005/0240116 A1 | 10/2005 | Saadat et al. | |
| 2006/0009715 A1 | 1/2006 | Khairkhahan et al. | |
| 2006/0085054 A1 | 4/2006 | Zikorus et al. | |
| 2006/0106375 A1 | 5/2006 | Werneth et al. | |
| 2006/0116609 A1 | 6/2006 | Kanuka et al. | |
| 2006/0201519 A1 | 9/2006 | Frazier et al. | |
| 2006/0241564 A1 * | 10/2006 | Corcoran | A61M 25/0138 604/523 |
| 2006/0282043 A1 * | 12/2006 | Pyles | A61M 25/0041 604/170.03 |
| 2006/0293697 A1 | 12/2006 | Nakao et al. | |
| 2007/0066968 A1 | 3/2007 | Rahn | |
| 2007/0118097 A1 | 5/2007 | Miller | |
| 2007/0118105 A1 | 5/2007 | Miller | |
| 2007/0135733 A1 | 6/2007 | Soukup et al. | |
| 2007/0179378 A1 | 8/2007 | Boese et al. | |
| 2007/0225701 A1 | 9/2007 | O'Sullivan | |
| 2007/0255183 A1 | 11/2007 | Chen | |
| 2008/0033415 A1 | 2/2008 | Rieker et al. | |
| 2008/0077126 A1 | 3/2008 | Rashidi | |
| 2008/0177175 A1 | 7/2008 | Mottola et al. | |
| 2008/0215047 A1 | 9/2008 | Calabro et al. | |
| 2008/0234606 A1 | 9/2008 | Itou | |
| 2008/0243112 A1 | 10/2008 | De Neve | |
| 2008/0272776 A1 | 11/2008 | Edelman | |
| 2008/0300590 A1 | 12/2008 | Horne et al. | |
| 2008/0306468 A1 | 12/2008 | Tamai et al. | |
| 2009/0030320 A1 | 1/2009 | Ishihara | |
| 2009/0112248 A1 | 4/2009 | Maloney | |
| 2009/0275956 A1 | 11/2009 | Burnes et al. | |
| 2009/0312602 A1 | 12/2009 | Sakamoto et al. | |
| 2010/0030098 A1 | 2/2010 | Fojtik | |
| 2010/0312223 A1 | 12/2010 | Kozak et al. | |
| 2012/0010524 A1 | 1/2012 | Fojtik et al. | |

FOREIGN PATENT DOCUMENTS

| | | |
|---|---|---|
| JP | 02-203835 A | 8/1990 |
| JP | HEI 03-056048 | 8/1991 |
| JP | 2002-541905 | 12/2002 |
| JP | 2005-503241 | 2/2005 |
| JP | 2005-095602 | 4/2005 |
| JP | 2005-270425 | 10/2005 |
| JP | 2007-537784 | 12/2007 |
| WO | 2000/062699 | 10/2000 |
| WO | 2002/043789 | 6/2002 |
| WO | 2005/117755 | 12/2005 |
| WO | 2006/055286 | 5/2006 |
| WO | 2007/001981 | 1/2007 |
| WO | 2009/117523 | 9/2009 |
| WO | 2012/151584 | 11/2012 |

OTHER PUBLICATIONS

State Intellectual Property Office of the People's Republic of China, Search Report, CN Application No. 201711418339.3, dated Sep. 26, 2018.

Japan Patent Office, Office Action, JP Application No. 2017-217984, dated Aug. 27, 2018.

European Patent Office, "Supplementary European Search Report," in European Patent Application No. 09721913.3, dated May 8, 2013.

Japanese Patent Office, "Final Notification of Reasons for Rejection," in Japanese Patent Application No. 2013-510314, dated Dec. 19, 2014.

Japanese Patent Office, "Reasons for Rejection," in Japanese Patent Application No. 2014-103146, dated Feb. 27, 2015.

United States Patent and Trademark Office as International Searching Authority, "International Search Report and Written Opinion" in related PCT application No. PCT/US2012/036814 dated Aug. 14, 2012.

Merriam-Webster's Collegiate Dictionary, 10th ed. Merriam-Webster, Inc. 2001. p. 449.

Sine wave, Revision as of Nov. 7, 2006, [online], [retrieved on Dec. 14, 2010]. Retrieved from Internet ,<URL: http://www.wikipedia.org>.

(56) References Cited

OTHER PUBLICATIONS

Ralph M. Hartwell II, "An Improved Sine to Square Wave Convertor for Rife/Bare Systems," May 24, 2001, [online], [retrieved on Mar. 24, 2011]. Retrieved from Internet, <URL: http://www.w5jgv.com>.

File:Waveforms.svg, Oct. 23, 2006, [online], [retrieved on Mar. 24, 2011]. Retrieved from Internet, <URL: http://www.wikipedia.org>.

File:Sine wave amplitude.svg, May 12, 2008, [online], [retrieved on Mar. 24, 2011]. Retrieved from Internet, <URL: http://www.wikipedia.org>.

* cited by examiner

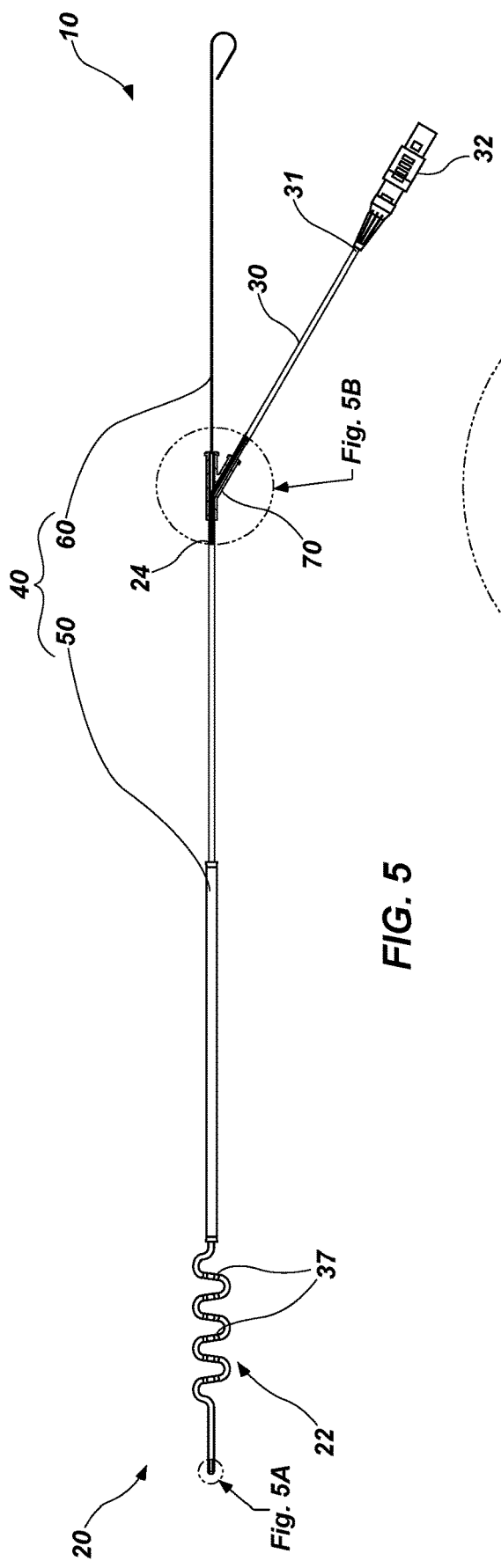
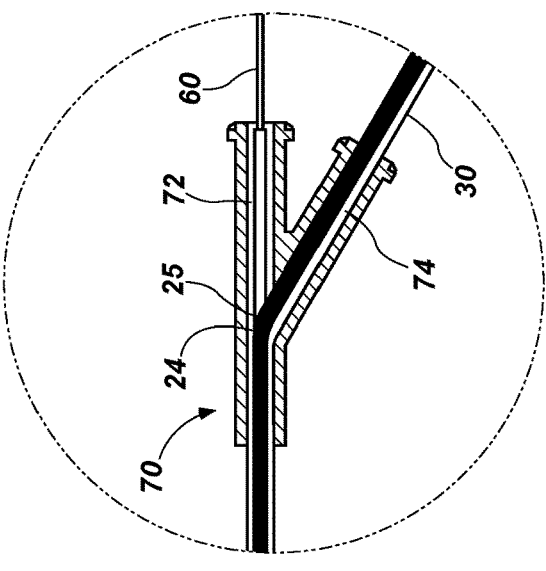
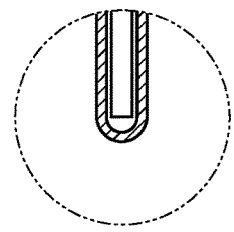
*FIG. 5*
*FIG. 5A*
*FIG. 5B*

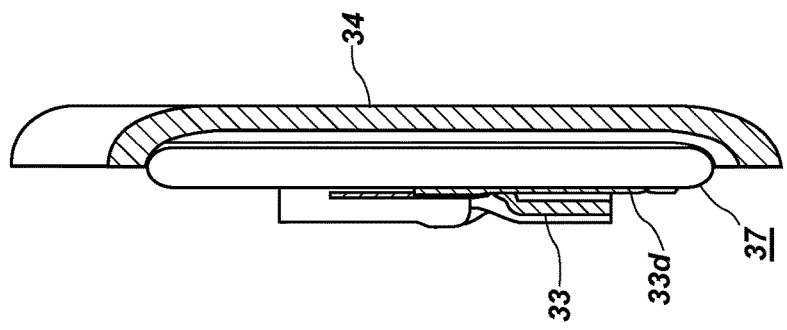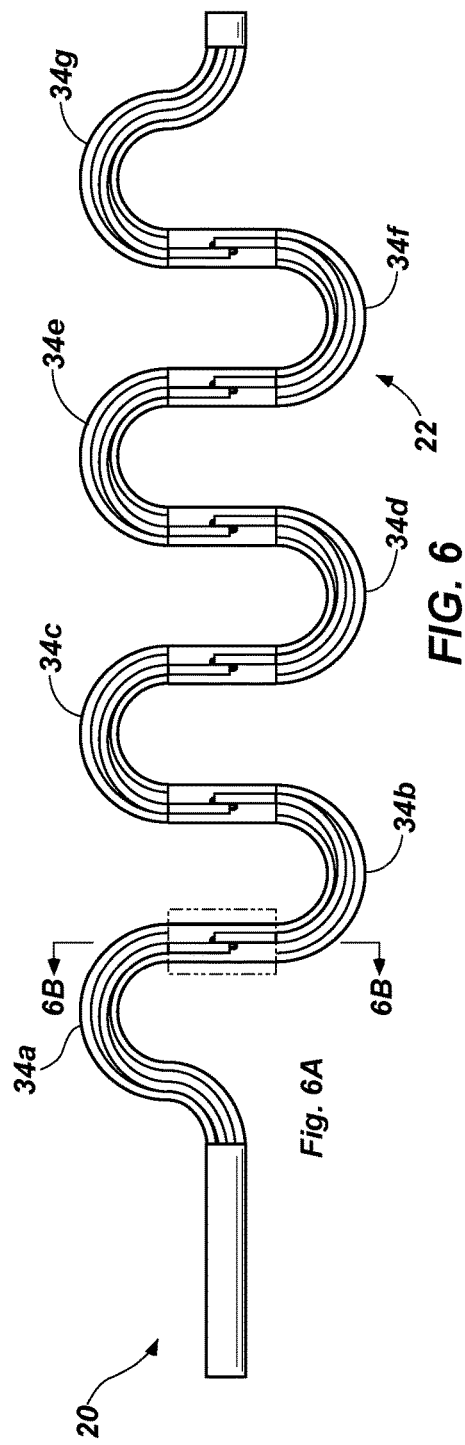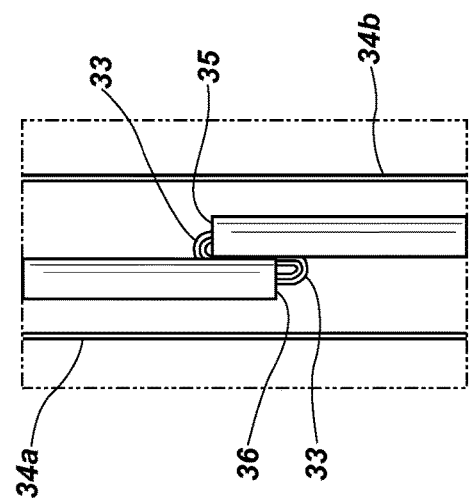

METHODS, APPARATUS AND SYSTEMS FOR FACILITATING INTRODUCTION OF SHAPED MEDICAL INSTRUMENTS INTO THE BODY OF A SUBJECT

CROSS-REFERENCE TO RELATED APPLICATIONS

This application is a continuation of U.S. patent application Ser. No. 13/101,640, filed on May 5, 2011, titled METHODS, APPARATUS AND SYSTEMS FOR FACILITATING INTRODUCTION OF SHAPED MEDICAL INSTRUMENTS INTO THE BODY OF A SUBJECT ("the '640 application"), issued as U.S. Pat. No. 9,833,149, on Dec. 5, 2017. The '640 application is a continuation-in-part of U.S. patent application Ser. No. 12/406,771, filed Mar. 18, 2009, titled LARGE SURFACE AREA TEMPERATURE SENSING DEVICE ("the '771 application"), issued as U.S. Pat. No. 9,155,476, on Oct. 13, 2015. The '771 application included a claim for priority under 35 U.S.C. § 119(e) to the Mar. 18, 2008 filing date of U.S. Provisional Patent Application 61/037,624.

TECHNICAL FIELD

The present invention relates generally to methods, apparatuses, and systems for introducing shaped medical instruments, such as catheters, into the body of a subject. More specifically, the present invention relates to methods, apparatuses, and systems for at least partially straightening or even substantially straightening shaped sections of medical instruments to facilitate their introduction into the body of a subject. Further, the present invention includes methods, apparatuses, and systems for facilitating the introduction of medical instruments into hollow organs to maximize or optimize contact with the interior surfaces of hollow organs or to change the shapes of (e.g., flatten, etc.) or otherwise manipulate the hollow organs.

SUMMARY

The present invention includes embodiments of methods, apparatuses, and systems that facilitate the introduction of shaped medical instruments into the body of a subject. Without limiting the scope of the present invention, methods and apparatus that incorporate teachings of the present invention are useful with a variety of different elongate medical instruments, including, but not limited to, esophageal temperature sensing catheters of the types disclosed by U.S. Provisional Patent Application No. 61/037,624, filed Mar. 18, 2008 (the "'624 Provisional application"), and U.S. patent application Ser. No. 12/406,771, filed Mar. 18, 2009 (the "'771 application"), the entire disclosures of both of which are, by this reference, hereby incorporated herein. Some embodiments of systems of the present invention may include elongate medical instruments of the types disclosed by the '624 Provisional application and the '771 application.

A method of the present invention may include applying external force to at least a shaped portion of a hollow, shaped elongate medical instrument (e.g., a catheter with a shaped portion, such as a serpentine portion of an esophageal temperature sensing catheter, etc.) to at least partially straighten, or even substantially straighten, the same. With the shaped portion of the elongate medical instrument at least partially straightened, a relatively rigid (when compared with the medical instrument), substantially linear or curvilinear internal element (e.g., a wire, etc.), or "retention element," may be introduced into an interior (e.g., a lumen, etc.) of the elongate medical instrument.

With the internal element in place, the external force may be removed. As the external force is removed, the internal element withstands or resists deformation under forces applied by the shaped portion of the elongate medical instrument and retains a somewhat linear configuration and/or applies force internally to at least the shaped portion, substantially retaining the shaped portion in the at least partially straightened configuration. While the configuration of the shaped portion may change somewhat as the external force is removed, the ability of the internal element to retain the shaped portion in a partially straightened configuration is considered, for purposes of this disclosure, to comprise substantial retention of the shaped portion in the at least partially straightened configuration.

The at least partially straightened configuration of the shaped portion of the elongate medical instrument facilitates its introduction into the body of a subject. In some embodiments, depending at least in part upon the relaxed shape of the shaped portion of the elongate medical instrument, at least partially straightening the shaped portion may reduce its effective width (i.e., the distance from one lateral extent of the entire shaped portion to the opposite lateral extent of the shaped portion), may minimize contact between the shaped portion and internal surfaces of any hollow organ into and/or through which the elongate medical instrument is introduced and/or may prevent the shaped portion from engaging, or grabbing onto, any part of any hollow organ into and/or through which the shaped portion is introduced.

Once the shaped portion of the elongate medical instrument has been positioned at an intended location within the interior of the hollow organ, the internal element may be removed from at least the interior of shaped portion of the elongate medical instrument. Removal of the internal element removes the internal force that holds the shaped portion in the at least partially straightened configuration, enabling the shaped portion to return to its relaxed, shaped configuration. As the shaped portion of the elongate medical instrument returns to its relaxed, shaped configuration, its contact with an interior surface of the hollow organ may increase or it may manipulate the shape of (e.g., flatten, etc.) the hollow organ.

In another aspect, the present invention includes straightening apparatus. A straightening apparatus of the present invention may least partially straighten a shaped portion of an elongate medical instrument. In some embodiments, such an apparatus includes an external element and a separate internal element.

The external element of a straightening apparatus may comprise a hollow elongate element with a length that will at least partially straighten a shaped portion of an elongate medical instrument (e.g., a curved portion of a medical instrument, such as the serpentine portions of various esophageal temperature sensing catheters disclosed in the '624 Provisional application and the '771 application, etc.). A passage through the external element may be configured to receive the elongate medical instrument. As the external element is translated (e.g., moved, slid, etc.) along the length of the elongate medical instrument and over the shaped portion, a wall of the external element exerts an external force against the shaped portion, causing it to at least partially straighten.

The internal element of the straightening apparatus, which is also referred to herein as a "retention element," may comprise an elongate element that is configured to fit within an interior (e.g., a lumen, etc.) of the elongate medical instrument and, thus, to be introduced into and at least temporarily reside within the interior of the elongate medical instrument. The internal element of the straightening apparatus may be relatively rigid when compared with the shaped portion of the elongate medical instrument. The relative rigidity of the internal element may enable the internal element to withstand force applied by the shaped portion of the elongate medical instrument, or to exert force against the shaped portion of the elongate medical instrument from within, which may hold the shaped portion in a partially straightened configuration while the internal element resides within the interior of the elongate medical instrument.

According to another aspect, the present invention includes a system for introducing an elongate medical instrument into the body of a subject. Such a system includes straightening apparatus, which may include an external element and an internal element, such as those described above, as well as an elongate medical instrument with which the external element and the internal element are configured to be used.

Other aspects, as well as features and advantages of various aspects, of the present invention will become apparent those of skill in the art through consideration of the ensuing description, the accompanying drawings and the appended claims.

BRIEF DESCRIPTION OF THE DRAWINGS

In the drawings,

FIGS. 5, 5A, and 5B depict the system shown in FIGS. 1 and 2, as well as other components that may be included in a system that incorporates teachings of the present invention;

FIGS. 6, 6A, 6B, and 6C illustrate a specific embodiment of elongate medical instrument with which a method and/or straightening apparatus (see, e.g., the embodiments of internal element and external element shown in FIGS. 3 and 4, respectively) of the present invention may be used.

DETAILED DESCRIPTION

Figure 1:
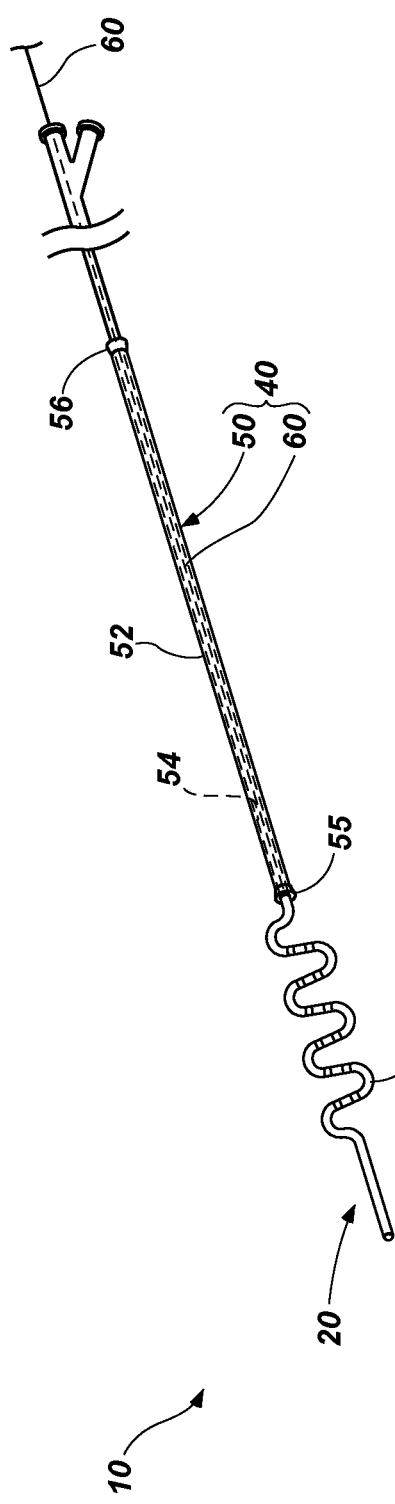
FIG. 1 depicts an embodiment of a straightening apparatus of the present invention, as well as a system that includes a straightening apparatus and an embodiment of an elongate medical instrument, with a shaped portion of the elongate medical instrument in a relaxed, or "pre-deployment," configuration.
Figure 2:
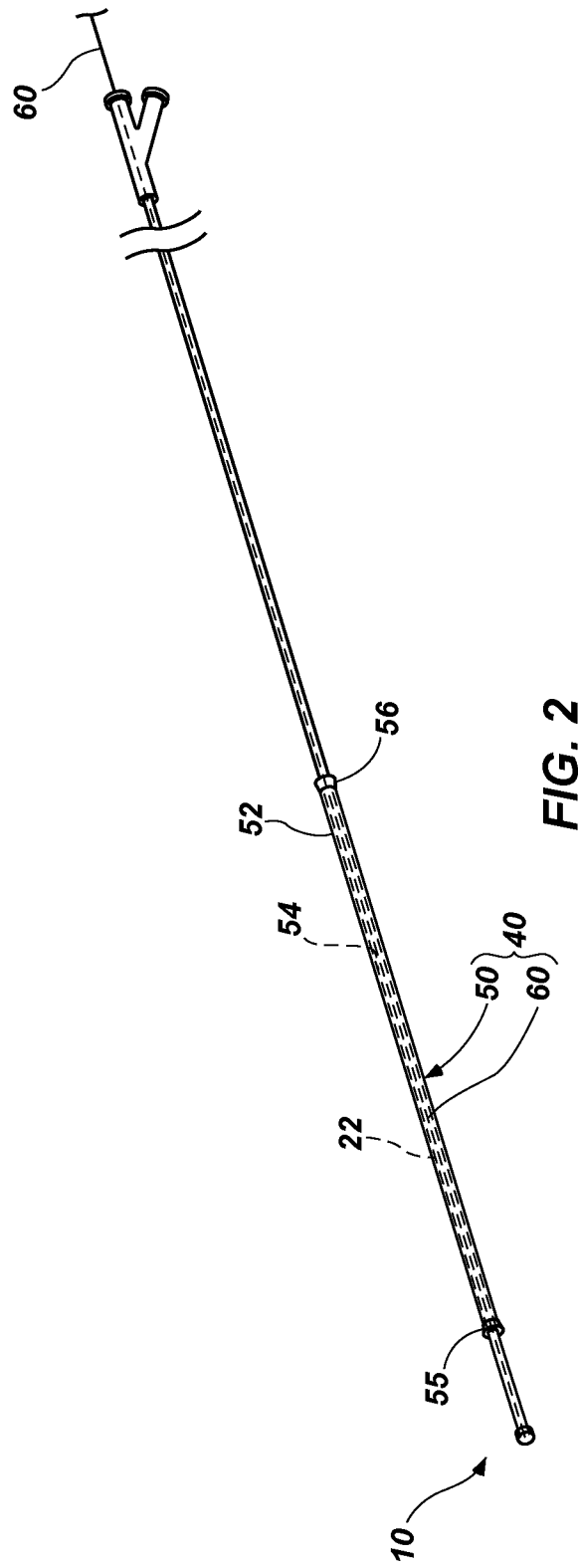
FIG. 2 illustrates the embodiment of straightening apparatus and system shown in FIG. 1, with the shaped portion of the elongate medical instrument in an at least partially straightened, or "deployment," configuration.

With reference to FIGS. 1 and 2, an embodiment of a system 10 for introducing an elongate medical instrument into a hollow organ of the body of a subject is illustrated. The system 10 shown in FIGS. 1 and 2 includes the medical instrument 20 and a straightening apparatus 40. In the depicted embodiment, the straightening apparatus 40 includes an external element 50 and an internal element 60.

Figure 3:
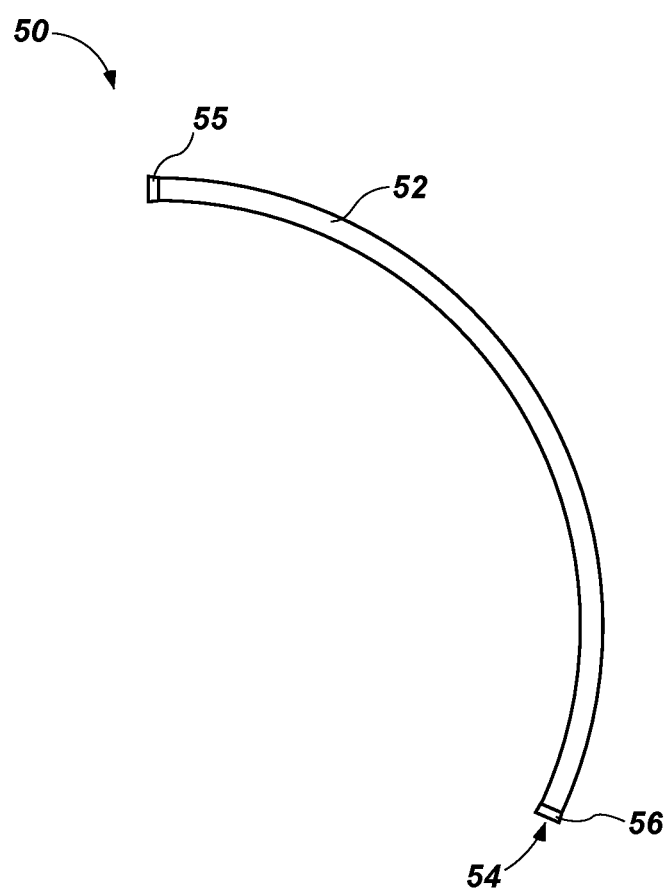
FIG. 3 depicts an embodiment of an external element of straightening apparatus.

With continued reference to FIGS. 1 and 2, and with added reference to FIG. 3, various features of an external element 50 of a straightening apparatus 40 (FIGS. 1 and 2) are described. In some embodiments, the external element 50 may be linear or substantially linear, while in other embodiments, it may have a curvilinear configuration.

The external element 50 may comprise an elongate element with an internal passage 54 defined by at least one outer wall 52. The passage 54 has dimensions large enough to enable it to receive a shaped portion 22 (FIGS. 1 and 2) of an elongate medical instrument 20 (FIGS. 1 and 2) and small enough to cause it to engage the shaped portion 22 to an extent sufficient to partially straighten or even substantially straighten the shaped portion 22 of the elongate medical instrument 20. The configuration of at least one outer wall 52 of the external element 50 and/or the material from which the at least one outer wall 52 is formed enable the at least one outer wall 52 to exert sufficient resistance against the shaped portion 22 to partially or substantially straighten the shaped portion 22 while the shaped portion 22 is positioned within the passage 54 and constrained by the outer wall 52 of the external element 50.

While the outer wall 52 of the external element 50 has a configuration and/or is formed from a material (e.g., polypropylene, etc.) that will enable it to partially or substantially straighten the shaped portion 22 of the medical instrument 20 (FIGS. 1 and 2), the exterior element 50 may be flexible enough to enable it, and any elongate medical instrument 20 and other components with which it is assembled, to be stored and/or transported in a coiled or otherwise compacted configuration. To illustrate this optional characteristic, the external element 50 is shown in FIG. 3 as having a curvilinear configuration.

Although FIGS. 1-3 show the external element 50 comprising a complete tube, other configurations of external elements are also within the scope of the present invention. In addition, external elements with incomplete configurations (e.g., configurations in which the outer wall 52 does not completely encompass the length of the passage 54, etc.) are within the scope of the present invention.

In some embodiments, the passage 54 of an external element 50 of a straightening apparatus 40 (FIGS. 1 and 2) of the present invention may include enlarged ends 55, 56. The enlarged ends 55 and 56 may be tapered to facilitate the introduction of an end (not shown) of a medical instrument 20 (FIGS. 1 and 2) therein.

Figure 4:
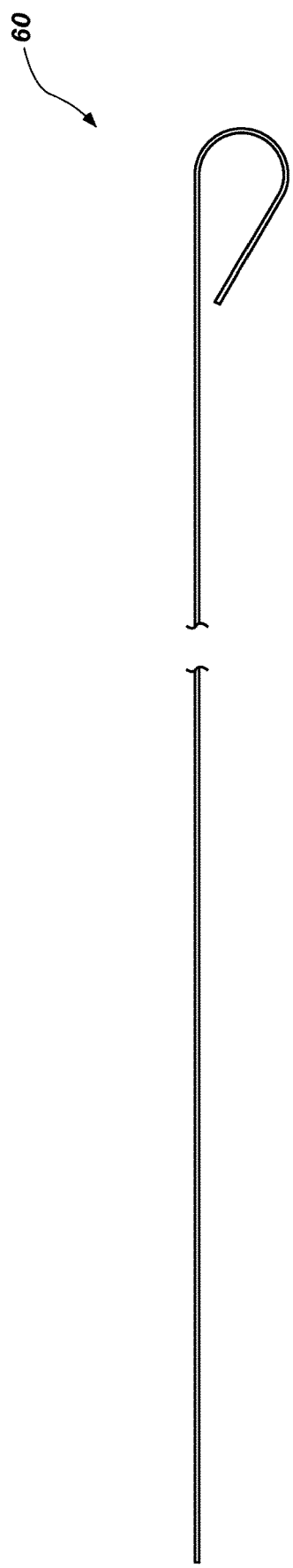
FIG. 4 depicts an embodiment of an internal element of straightening apparatus.

Turning now to FIG. 4, while maintaining reference to FIGS. 1 and 2, an internal element 60, or "retention element," of a straightening apparatus 40 of the present invention may include an elongate element that may be introduced into and reside within an interior (e.g., a lumen, etc.) of the medical instrument 20 (FIGS. 1 and 2), including its shaped portion 22. One or both of the configuration of the internal element 60 and/or the materials from which the internal element 60 is formed (e.g., stainless steel, etc.) impart it with sufficient rigidity to resist bending when disposed within the interior of the shaped portion 22 and, thus, to retain the shaped portion 22 in an at least partially straightened or substantially straightened configuration.

In the embodiment illustrated by FIG. 4, the internal element 60 comprises a wire, or stylet. In various embodiments, an internal element 60 that comprises a wire, or stylet, may include a single filament, a coiled filament surrounding a linear or substantially linear (e.g., curvilinear, etc.) core, a plurality of twisted or woven filaments or any other suitable configuration. In particular, the illustrated embodiment of internal element 60 comprises a single filament wire with a 0.023 inch diameter.

Turning now to FIGS. 5 through 5B, an additional, optional feature of a system 10 that incorporates teachings of the present invention is depicted. Specifically, the embodiment of system 10 shown in FIGS. 5 and 5B includes a branched connector 70 (e.g., a Y-connector, a T-connector, etc.), which is configured to be positioned at or adjacent to a proximal and 24 of the medical instrument 20. A branched connector 70 may include a plurality of ports 72, 74 that are configured to communicate with a lumen 25 and/or other features of the medical instrument 70. As illustrated, one port 72 of the branched connector 70 may be configured to receive a portion of the internal element 60 of the straightening apparatus 40, while another port 74 of the branched connector 70 may be configured to enable control over another functionality of the elongate medical instrument 20. In embodiments where the elongate medical instrument 20 comprises an esophageal temperature sensing catheter or other temperature sensing device, the other port 74 may be configured to receive a thermistor cable 30 that extends into the elongate medical instrument 20.

Figure 6C:
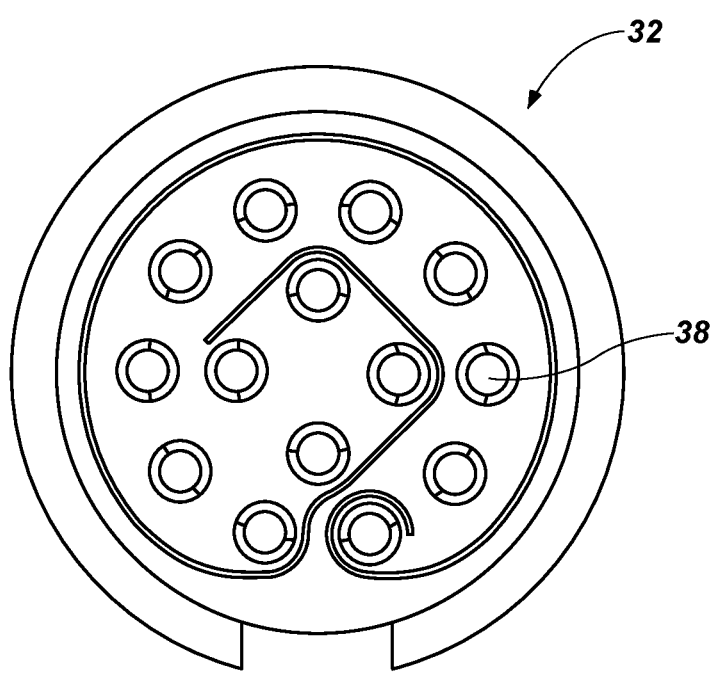

FIG. 5 also depicts the elongate medical instrument 20 as including an embodiment of a connector 32 at a proximal end 31 of the thermistor cable 30. Other features of a specific embodiment of medical instrument 20 are shown in FIGS. 6 through 6C. Specifically, FIGS. 6 through 6C show an example of a configuration for a thermistor cable 30. The depicted embodiment of thermistor cable 30 includes at least thirteen (13) electrically isolated filaments, or wires 33. In addition, the depicted thermistor cable 30 includes seven (7) segments 34 (34a, 34b, 34c, etc.), with the ends 35, 36 of adjacent segments 34 overlapping each other. The number of wires 33 and the number of segments 34 is at least partially dependent upon the desired number of thermistor contacts or bands, or, more simply "thermistors" 37 (FIG. 5), for a particular medical instrument 20 (e.g., there are twelve (12) thermistor contacts 37 in the depicted embodiment, etc.). In the depicted embodiment, one of the thirteen wires 33 is a common wire that communicates with each of the thermistors 37, while each of the other wires 33 communicates with a single thermistor 37, or is a "thermistor-specific" wire. At each overlap location, at least some of the wires 33 emerge from the end 36 of one segment 34 (e.g., segment 34a, etc.) and extend into the adjacent end 35 of the next segment 34 (e.g., segment 34b, etc.). As shown in FIG. 6B, at that overlap location, a distal end 33d of one thermistor-specific wire 33 and a looped portion of the common wire 33 extend back toward the segment 34 (e.g., segment 34a, etc.) from which it emerged, while another thermistor-specific wire 33 and another looped portion of the common wire 33 extend in the opposite direction, toward or along the next segment (e.g., segment 34b, etc.). The distal end 33d of each thermistor-specific wire 33 and an exposed region of the looped portion of the common wire 33 that corresponds to each thermistor-specific wire 33 are electrically coupled to a corresponding thermistor 37 (FIG. 5), which is exposed to an exterior surface of the shaped portion 22 of the elongate medical instrument 20.

FIG. 6C depicts an embodiment of a connector 32 and pin 38 layout that may be used with a thermistor cable 30 (FIGS. 5 and 5B) of the embodiment of medical instrument 20 depicted by FIGS. 6 through 6B. The connector 32 is located at the proximal end of the thermistor cable 30, with each pin 38 being electrically coupled to the proximal end (not shown) of each wire 33 of the thermistor cable 30.

In some embodiments, the elongate medical instrument 20 may be at least partially radio-opaque. At least the shaped portion 22 of an at least partially radio-opaque elongate medical instrument 20 may be formed from a radio-opaque material, or it may include one or more radio-opaque features.

Figure 7B:
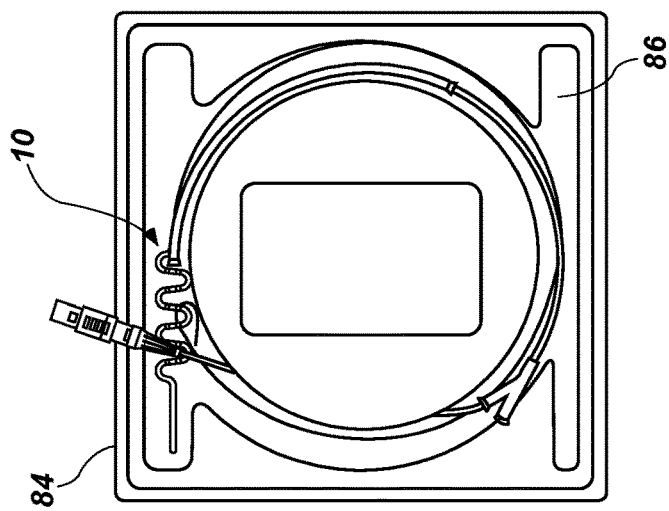
FIGS. 7A and 7B show an embodiment of a packaged system of the present invention.
Figure 7A:
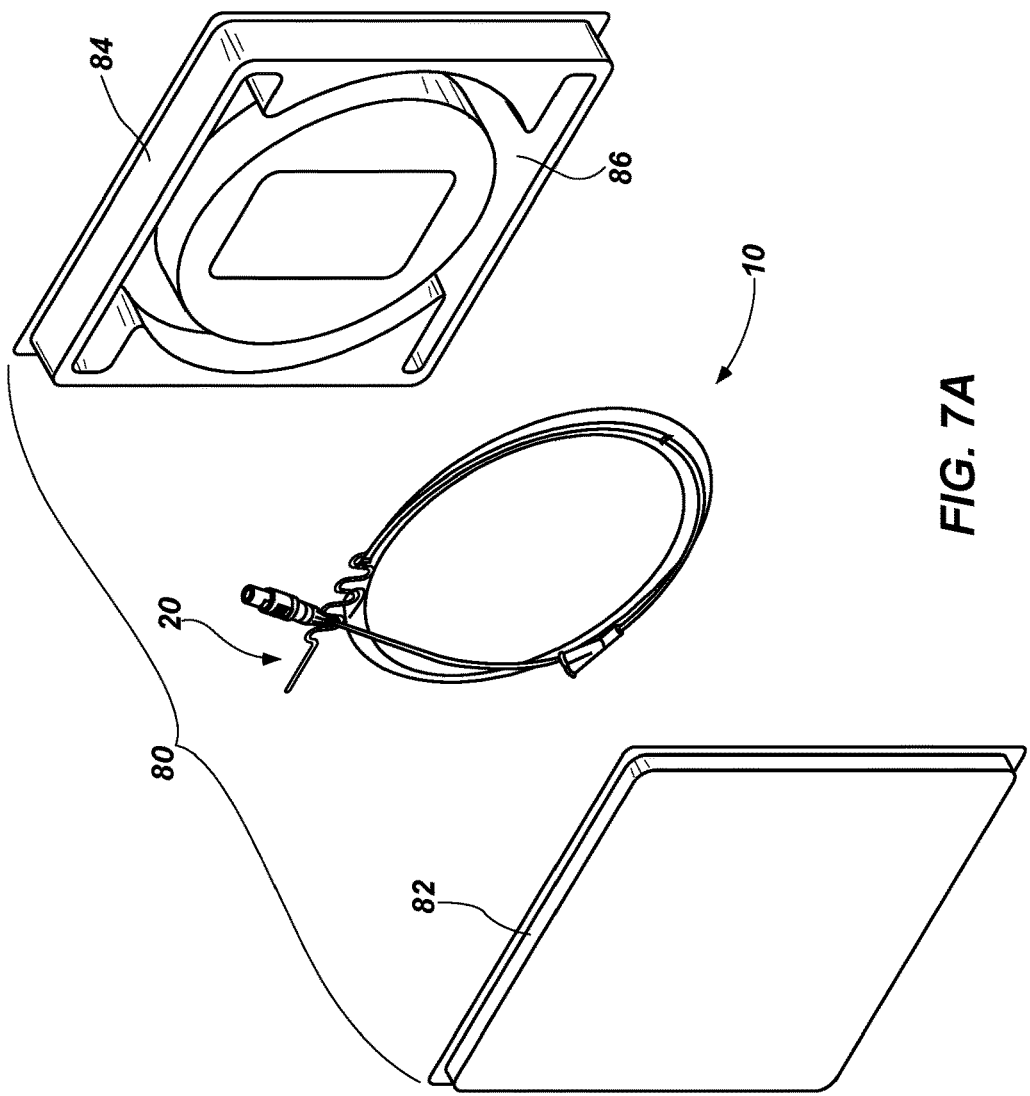

In FIGS. 7A and 7B, an embodiment of a package 80 is shown. The illustrated embodiment of package 80 includes a base 84 and a cover 82. As shown, the base 84 may include a receptacle 86 for receiving a system 10 (see, e.g., FIG. 5) that incorporates teachings of the present invention. More specifically, the receptacle 86 may be configured to receive the system 10 with the elongate medical instrument 20 thereof in a compact configuration, such as the depicted coil. The cover 82 may be configured for assembly with the base 84 and, thus, to at least partially retain a system 10 within the receptacle 86 of the base 84.

In the depicted embodiment, the base 84 and cover 82 of the package 80 comprise molded elements. Of course, other embodiments of packages are also within the scope of the present invention.

When use of an elongate medical instrument 20 with a shaped portion 22 is desired, a system 10 that includes the elongate medical instrument 20 may be removed from its package 80. The system 10 may be visually inspected for damage, kinks, debris, and missing components. In some embodiments, functionality of the elongate medical instrument 20 may be tested before its introduction into the body of a subject. Use of the system 10 may be continued if no defects are observed.

With the system 10 in hand, an external force may be applied to at least the shaped portion 22 of the elongate medical instrument 20. In some embodiments, this act may be accomplished with an external element 50 of a straightening apparatus 40, which may be pre-assembled with the elongate medical instrument 20, as shown in FIG. 1. The external element 50 may be positioned (e.g., moved distally along the elongate medical instrument shown in FIG. 1, etc.) over at least a portion of the shaped portion 22 of the elongate medical instrument 20, as depicted by FIG. 2.

With the shaped portion 22 of the elongate medical instrument 20 at least partially straightened, a relatively rigid (when compared with the elongate medical instrument), substantially linear or curvilinear internal element 60 may be introduced into at least part of the interior of the shaped portion 22. FIG. 2 illustrates an embodiment of such an internal element 60. The internal element 60 may also come preassembled with the elongate medical instrument 20, as depicted by FIGS. 7A and 7B. In the illustrated embodiment, the act of introducing the internal element 60 at least partially into the shaped portion 22 of the elongate medical instrument 20 may be effected by grasping a proximal end of the internal element 60 and moving the internal element 60 distally into the interior of the shaped portion 22. In some embodiments, the distance the internal element 60 is moved may be limited by a feature at or near a proximal end of the internal element 60.

With the internal element in place within at least part of the shaped portion 22, the external force (e.g., that applied by the external element 50, etc.) may be removed. As the external force is removed, the internal element 60 withstands or resists the tendency of the shaped portion 22 to return to its relaxed, shaped configuration and, therefore, retains the shaped portion 22 the at least partially straightened or substantially straightened configuration.

The at least partially straightened configuration or substantially straightened configuration of the shaped portion 22 of the elongate medical instrument 20 facilitates its introduction into the body of a subject. In some embodiments, depending at least in part the relaxed shape of the shaped portion 22 of the elongate medical instrument 20, at least partially straightening a shaped portion of the elongate medical instrument 20 may reduce the effective width of the shaped portion 22, may minimize contact between the shaped portion 22 and internal surfaces of any organ into and/or through which the elongate medical instrument 20 is introduced and/or may prevent the shaped portion 22 of the elongate medical instrument 20 from engaging, or grabbing onto, any part of any organ into and/or through which the elongate medical instrument 20 is introduced.

Before introducing the elongate medical instrument 20 into the body of a subject, a lubricant (e.g., a water soluble material, etc.) may be applied to at least the shaped portion 22. Introduction of the shaped portion 22 of the elongate medical instrument 20 into the interior of a hollow organ may be effected with visual guidance; for example, under fluoroscopic x-ray. The use of visual guidance may prevent damage to a subject's body during introduction of the shaped portion 20 into the hollow organ.

Once the shaped portion 20 of the elongate medical instrument 20 has been positioned at an intended location within the interior of the hollow organ, the internal element 60 may be removed from the interior of the shaped portion 22 and, optionally, from the interior of the entire elongate medical instrument 20. Removal of the internal element 60 removes the internal force that holds the shaped portion 22 in the at least partially straightened or substantially straightened configuration, enabling the shaped portion 22 to return to its relaxed, shaped configuration, such as that depicted by FIG. 1. As the shaped portion 22 of the elongate medical instrument 20 returns to its relaxed, shaped configuration, it may manipulate the shape of (e.g., flatten, etc.) the hollow organ. The position of the shaped portion 22 within the interior of the hollow organ may be viewed under fluoroscopic x-ray and, if necessary, changed.

In embodiments where operation of the elongate medical instrument 20 requires assembly of the elongate medical instrument 20 with an exterior apparatus, such assembly may be effected. Without limiting the scope of the present invention, when the elongate medical instrument 20 comprises a temperature sensing device, such as an esophageal temperature sensing catheter, thermistors, or other temperature sensing elements of the elongate medical instrument may be electrically coupled to an appropriate sensor.

Once use of the elongate medical instrument 20 is complete, it may be disconnected from any exterior apparatus. Depending upon the type of elongate medical instrument 20 used, it may be discarded or cleaned and sterilized for subsequent use.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie within the scopes of the invention and the appended claims. Features from different embodiments may be employed in combination. The scope of the invention is indicated and limited only by the appended claims and their legal equivalents. All additions, deletions and modifications to the invention, as disclosed herein, that fall within the meaning and scopes of the claims are to be embraced thereby.

What is claimed:

1. An apparatus for straightening a shaped portion of an elongate medical instrument, comprising:
   an internal element including an elongate element that retains the shaped portion of the elongate medical instrument in an at least partially straightened configuration while present within a lumen that extends through a length of the elongate medical instrument:
      without assistance of external force on the shaped portion of the elongate medical instrument from an exterior of the shaped portion of the elongate medical instrument; and
      while the shaped portion of the elongate medical instrument is introduced into a hollow organ of a subject,
   the internal element being completely removable from the lumen of the elongate medical instrument.

2. The apparatus of claim 1, wherein the internal element is capable of retaining a tortuous shaped portion of the elongate medical instrument in an at least partially straightened configuration.

3. The apparatus of claim 2, wherein the internal element is capable of retaining a serpentine portion of the elongate medical instrument in an at least partially straightened configuration.

4. The apparatus of claim 1, wherein the internal element has a length sufficient to reside within an entirety of the shaped portion of the elongate medical instrument.

5. The apparatus of claim 1, wherein the internal element is substantially linear.

6. The apparatus of claim 1, wherein the internal element is curvilinear.

7. The apparatus of claim 1, wherein the internal element comprises a wire.

8. The apparatus of claim 1, wherein a rigidity of the internal element exceeds a rigidity of at least the shaped portion of the elongate medical instrument.

9. An apparatus for straightening a shaped portion of an elongate medical instrument, comprising:
   an internal element:
      comprising an elongate element having sufficient flexibility to follow a curvilinear path but having sufficient rigidity to resist conformation to a shape of the shaped portion of the elongate medical instrument;
      positionable within a portion of a lumen of the elongated medical instrument extending through the shaped portion of the elongate medical instrument to place the shaped portion of the elongate medical instrument in an at least partially straightened configuration and removable from the lumen of the elongated medical instrument to enable the shaped portion of the elongate medical instrument to assume a relaxed configuration; and
      the internal element holding the shaped portion of the elongate medical instrument in the at least partially straightened configuration:
         without assistance of external force on an exterior of the shaped portion of the elongate medical instrument; and
         while the shaped portion of the elongate medical instrument is introduced into a body of a subject.

10. The apparatus of claim 9, wherein the internal element at least partially places the shaped portion of the elongate medical instrument in the at least partially straightened configuration upon advancement of the internal element into the portion of the lumen of the elongate medical instrument extending through the shaped portion.

11. The apparatus of claim 9, wherein the internal element has a length sufficient to reside within an entirety of the shaped portion of the elongate medical instrument in the at least partially straightened configuration.

12. The apparatus of claim 9, wherein the internal element is substantially curvilinear.

13. The apparatus of claim 9, wherein the internal element is substantially linear.

14. A method for introducing a shaped portion of an elongate medical instrument into a hollow interior of an internal organ of a body of a subject, comprising:
- advancing an elongate element into an interior of the shaped portion of the elongate medical instrument to retain the shaped portion of the elongate medical instrument in an at least partially straightened configuration without application of an external force to the shaped portion of the elongate medical instrument;
- introducing at least the shaped portion of the elongate medical instrument into a hollow interior of an internal organ of a body of a subject while the elongate element resides within the interior of the shaped portion of the elongate medical instrument; and
- withdrawing the elongate element from the interior of the elongate medical instrument and enabling the shaped portion to assume a desired shape within the hollow interior of the internal organ.

15. The method of claim 14, wherein enabling the shaped portion of the elongate medical instrument to assume the desired shape comprises causing at least part of the shaped portion of the elongate medical instrument to contact in inner surface of the internal organ.

16. The method of claim 14, wherein enabling the shaped portion of the elongate medical instrument to assume the desired shape comprises causing at least part of the shaped portion of the elongate medical instrument to modify a shape of the internal organ.

17. The method of claim 14, wherein introducing the elongate element comprises introducing the elongate element into an entirety of the interior of the shaped portion of the elongate medical instrument.

18. The method of claim 14, wherein introducing the elongate element comprises introducing a wire into the interior of the shaped portion of the elongate medical instrument.

19. The method of claim 14, wherein withdrawing the elongate element comprises withdrawing an entirety of the elongate element from the interior of the elongate medical instrument.

* * * * *